United States Patent [19]

Gerdes

[11] Patent Number: 4,743,345
[45] Date of Patent: May 10, 1988

[54] APPARATUS FOR AND METHOD OF OPERATING A HYGROMETER IN A REPETITIVE BATCH TITRATION MODE

[75] Inventor: Walter F. Gerdes, Lake Jackson, Tex.
[73] Assignee: The Dow Chemical Company, Midland, Mich.
[21] Appl. No.: 760,207
[22] Filed: Jul. 29, 1985
[51] Int. Cl.$^4$ ............................................. G01N 27/42
[52] U.S. Cl. ................................. 204/1 T; 204/406; 204/430
[58] Field of Search ....................... 204/1 W, 430, 406

[56] References Cited

U.S. PATENT DOCUMENTS

| | | | |
|---|---|---|---|
| 3,051,643 | 8/1962 | Bergson | 204/409 |
| 3,146,181 | 8/1964 | Bell | 204/406 |
| 3,244,602 | 4/1966 | Glass et al. | 204/1 T |
| 3,823,082 | 7/1974 | Czuha, Jr. | 204/430 |

OTHER PUBLICATIONS

F. A. Keidel, Anal. Chem., vol. 31, No. 12, pp. 2043-2048, Dec. 1959.

*Primary Examiner*—G. L. Kaplan

[57] ABSTRACT

A method of operating electrolytic hygrometers in a batch mode that substantially reduces the time required for electrolysis. A substantially constant amount of moisture is retained in the hygrometer between samples by controlling the electrolysis current. Preferably, the electrolysis current is also limited to a predetermined value to reduce moisture gradients within the hygrometer and thus improve the accuracy of the analysis.

8 Claims, 1 Drawing Sheet

APPARATUS FOR AND METHOD OF OPERATING A HYGROMETER IN A REPETITIVE BATCH TITRATION MODE

FIELD OF THE INVENTION

This invention relates generally to moisture analyzers and more particularly to the operation of electrolytic hygrometers.

BACKGROUND OF THE INVENTION

The presence of water in small quantities in gaseous hydrocarbons is harmful to industrial processes and the monitoring of moisture content is necessary to assure proper results. The aluminum oxide electrolytic hygrometer is very good for measuring very low levels of moisture in gases and some liquids if the sample is not harmful toward aluminum or aluminum oxide. The $P_2O_5$ electrolytic hygrometer is somewhat less sensitive but very useful for many more harmful gas samples encountered in chemical plants. However, some samples are disruptive of the $P_2O_5$ hygrometer. HCl in concentration above 1% gives a background reading because the HCl is partially electrolyzed. For such samples that contain very low ranges of moisture, the signal from the $P_2O_5$ hygrometer is low and subject to considerable uncertainty. The levels of moisture which are the concern generally are in the range of 2 to 50 parts per million (ppm).

U.S. Pat. No. 3,244,602 discloses the operation of an electrolytic hygrometer in a repetitive batch titration mode to detect low levels of moisture. A gas sample passes through the hygrometer while it is deenergized such that the hygroscopic material absorbs the moisture from the gas sample. Following a purge of the system, the hygrometer is energized and electrolyzes moisture absorbed from the gas sample. The length of the electrolysis is arbitrarily selected to assure that substantially all of the moisture will be electrolyzed. The moisture content of the gas sample can be calculated from the current-time integral (microampere-minutes) used to electrolyze the moisture as described in U.S. Pat. No. 2,830,945 which describes a continuous operation of electrolytic hygrometers.

Electrolytic hygrometers are generally operated in a continuous mode, rather than in the repetitive batch titration mode because of the time required to electrolyze substantially all of the water absorbed from a gas sample. For example, a typical electrolysis time of 20 minutes is indicated in FIG. 3A for the repetitive batch titration mode hygrometer of U.S. Pat. No. 3,244,602. As a result, increases in the moisture level of hydrocarbon streams would go undetected for at least 20 minutes even if other steps in the analysis could be reduced to a minimum.

SUMMARY OF THE INVENTION

The present invention is a method of operating electrolytic hygrometers in a repetitive batch titration mode such that the electrolysis time is reduced to a few minutes. The invention can be described as a method for determining the moisture content of a gas stream having a low level of moisture, comprising the steps of passing a measurable volume of the gas stream through a confined space containing a hygroscopic material that contains an arbitrary initial amount of moisture, substantially absorbing the moisture from the volume with the hygroscopic material, passing an electrolysis current through the hygroscopic material after the moisture from the volume is absorbed, and terminating the electrolysis current when the moisture contained by the hygroscopic material decreases to substantially the initial amount of moisture.

FIG. 1 schematically shows a moisture analyzer employing the subject invention.

DETAILED DESCRIPTION OF THE INVENTION

Figure 1:
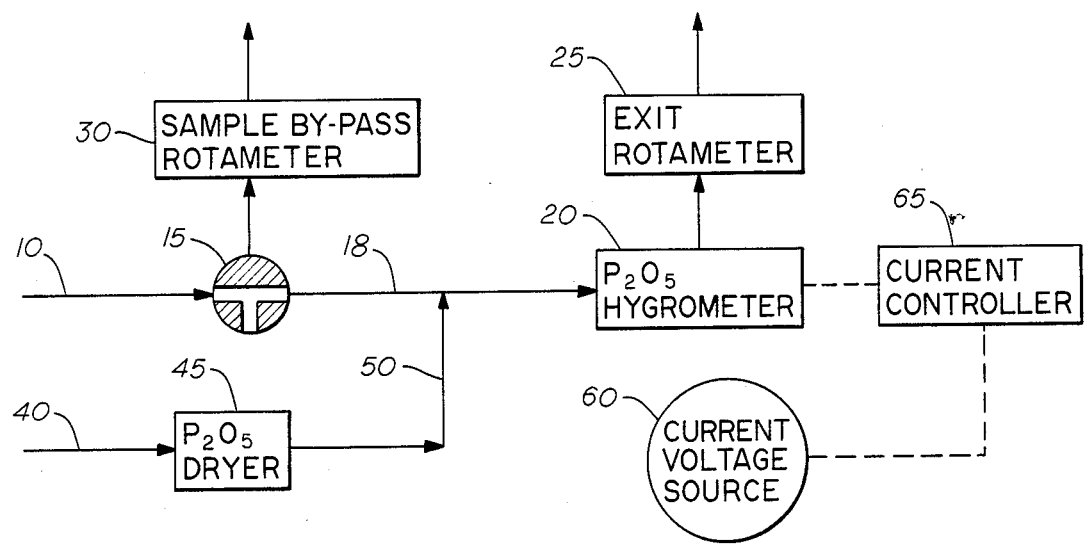

The subject invention can be practiced using any hygrometer that employs a hygroscopic material by operating the hygrometer in a batch titration mode such that a substantially constant amount of moisture remains within the hygrometer after the electrolysis of each sample. A preferred system, shown in FIG. 1, maintains the substantially constant amount of moisture within a $P_2O_5$ hygrometer by controlling the electrolysis current.

In FIG. 1, a gas sample 10 of unknown water content passes through a 3-way solenoid valve 15, through line 18, through a $P_2O_5$ hygrometer 20 containing an arbitrary initial amount of moisture and through a flow meter 25. While in this configuration, substantially all of the moisture from the gas sample 10 is absorbed by the $P_2O_5$ hygrometer 20 such that the flow meter 25 actually monitors the flow rate of dry sample gas 10.

The hygrometer 20 is preferably de-energized while the sample gas passes through the hygrometer. Alternatively, a low electrolysis current can be passed through the hygrometer 20 if the current does not significantly decompose the absorbed moisture at this time.

A timer (not shown) controls the volume of the gas sample 10 that passes through the hygrometer 20 by switching the configuration of the valve 15 at a predetermined time. A sample volume of 200 milliliters is preferred for samples estimated to contain between 20 and 50 ppm of water and for $P_2O_5$ hygrometers designed for a flow rate of about 100 milliliters per minute. For a flow rate of 100 milliliters per minute, the timer would be set to switch valve 15 about 2 minutes after the sample gas 10 was connected to the hygrometer 20. In the alternate configuration of valve 15 (not shown), the sample gas 10 passes through valve 15 and through a flow meter 30 that monitors the sample gas flow including moisture.

While the sample gas 10 passes through the hygrometer 20 as shown in FIG. 1, a small amount of a purge gas 40 passes through a $P_2O_5$ dryer 45, through line 50 and into line 18 in order to prevent moisture from entering the hygrometer through any leaks in these purge gas components. When the timer switches the configuration of valve 15, the timer also activates a valve (not shown) to substantially increase the flow rate of the purge gas 40 which then purges the remaining sample gas 10 from the hygrometer 20. The timer also controls the length of the purge which is typically about 15 seconds for a $P_2O_5$ hygrometer designed for a flow rate of about 100 milliliters per minute. At the end of the purge of the hygrometer 20, the timer substantially increases the electrolysis current to the hygrometer 20 and activates any recording and calculating equipment (not shown) that records and calculates the energy required for electrolysis.

The electrolysis current is provided by a constant voltage source 60 which is connected to the hygrometer 20 through a current controller 65. A constant voltage source of 45 volts is typically used with a $P_2O_5$ hygrometer designed for a flow rate of about 100 milliliters per minute. During the continuous operation of the $P_2O_5$ hygrometer according to prior art mentioned above, the voltage source is connected directly to the hygrometer and the current is limited only by the resistance of the wet hygroscopic material within the hygrometer. However, the current controller 65 of the present batch mode titration maximum current being sent to the hygrometer 20 to a predetermined value, preferably about 250 microamps for samples estimated to contain between 2 and 50 ppm of water.

The electrolysis current remains at the predetermined limiting value until the voltage source 60 can no longer maintain that amount of current through the hygrometer 20 as a result of the drying of the hygroscopic material. Then the current decreases as accumulated moisture is further reduced by electrolysis. When the current drops to a predetermined value, preferably about 100 microamps, that corresponds to the arbitrary initial amount of moisture contained within the hygrometer, the current controller 65 substantially reduces the current passing to the hygrometer 20 to a predetermined value, preferably zero.

Limiting the electrolysis current as described enhances the accuracy of the analysis. When a continuous hygrometer is operated in a repetitive batch titration mode, the level of current passing through the hygrometer varies in an unknown relationship to the amount of moisture contained within the hygrometer. This relationship is not easily described since the electrolysis current tends to form moisture gradients within the hygroscopic material. Limiting the initial current controls the size of the moisture gradients so that the gradients are less likely to vary significantly from one analysis to the next. As a result, the electrolysis can be terminated at a specific current level with improved confidence that the specific current level approximates a constant amount of moisture within the hygroscopic material.

The length of the electrolysis step varies depending upon the amount of moisture contained within the hygrometer 20. A large portion of the moisture within the hygrometer is electrolyzed at a steady rate as a result of limiting the current. Regardless of the amount of moisture absorbed from a sample, the moisture level within the hygrometer decreases at a constant rate to an arbitrary level which can be defined as the amount of moisture that would initially give the maximum current permitted by the current controller 65. Once this point is obtained, the current to the hygrometer 20 is allowed to decrease as the moisture within the hygrometer decreases until the current reaches the predetermined value corresponding to the arbitrary initial amount of moisture.

Following the procedure described above, a substantially constant amount of moisture remains in the hygrometer at the termination of each electrolysis such that the amount of moisture removed from the gas sample is substantially equal to the amount of moisture that is electrolyzed. Using the electrochemical equivalence factor for water, 0.005601 micrograms of water per microamp per minute, the amount of moisture removed by electrolysis from the hygrometer can be calculated from the microampere minutes used for electrolysis.

The time typically required for electrolysis using the above-described method is about 3 minutes and an entire cycle including absorption and purging can be performed in about 5 minutes. The substantial reduction in electrolysis time over the prior art is achieved by not electrolyzing substantially all of the moisture from the hygrometer since the rate of electrolysis decreases rapidly as the hygroscopic material dries.

The method described above achieves an arbitrary initial amount of moisture within the hygrometer before each analysis by terminating the electrolysis at a current level substantially equivalent to the arbitrary amount of moisture. In some situations, hygrometers may absorb sample constituents that do not readily electrolyze causing a shift in the level of current that corresponds to the arbitrary initial amount of moisture. In such situations, the subject method would be improved by terminating the electrolysis current at the occurrence of some event other than a predetermined current level if that event corresponds to the arbitrary initial amount of moisture. An example would be terminating the electrolysis current when the rate of decrease in the current reaches an arbitrary value if this value better corresponds to the arbitrary initial amount of moisture.

What is claimed is:

1. A method for determining the moisture content of a gas stream having a low level of moisture, comprising the steps of:
    substantially absorbing the moisture from a measurable volume of gas stream with a hygroscopic material;
    electrolyzing a large portion of the moisture within the hygroscopic material at a steady rate with an electrolysis current that is generated by a constant voltage source connected to a current controller, the electrolysis current being limited to a predetermined value by the current controller until the voltage source can no longer maintain the current at the predetermined value; and
    passing the electrolysis current through the hygroscopic material at a decreasing level until the current drops to a predetermined low value.

2. The method of claim 1 wherein the hygroscopic material is $P_2O_5$.

3. The method of claim 1 further comprising the step of calculating the moisture content of the gas stream from a current-time integral of the electrolysis current.

4. The method of claim 1 wherein the electrolysis current is maintained at a predetermined value of about 250 microamps before the current decreases.

5. The method of claim 4 wherein the current decreases to a predetermined low value of about 100 microamps.

6. An apparatus for determining the moisture content of a gas stream having a low level of moisture, comprising:
    means for substantially absorbing the moisture from a measurable volume of the gas stream with a hygroscopic material;
    means for passing an electrolysis current through the hygroscopic material at a predetermined value including a constant voltage source connected to a current controller for maintaining the current at the predetermined value during electrolysis of a large portion of the moisture within the hygroscopic material; and
    means for passing the electrolysis current through the hygroscopic material at a decreasing level until the current drops to a predetermined low value.

7. The apparatus of claim 6 wherein the hygroscopic material is $P_2O_5$.

8. The apparatus of claim 6 further comprising means for calculating the moisture content of the gas stream from a current-time integral of the electrolysis current.

* * * * *